United States Patent [19]

Haginaka et al.

[11] Patent Number: 5,670,629

[45] Date of Patent: Sep. 23, 1997

[54] OVOGLYCOPROTEIN AND AGENTS FOR CHROMATOGRAPHIC SEPARATION CONTAINING SAME

[75] Inventors: Jun Haginaka; Hiroo Wada; Hiroya Fujima, all of Kyoto, Japan

[73] Assignee: Shinwa Chemical Industries, Ltd., Kyoto, Japan

[21] Appl. No.: 397,861

[22] Filed: Mar. 2, 1995

[30] Foreign Application Priority Data

Nov. 1, 1994 [JP] Japan .................................. 6-269073

[51] Int. Cl.$^6$ .................................. C07K 1/00; A23J 1/00
[52] U.S. Cl. .................. 530/395; 530/326; 530/367; 530/368; 530/412; 530/416; 530/427; 530/827
[58] Field of Search ........................ 530/395, 326, 530/367, 368, 412, 416, 427, 827

[56] References Cited

PUBLICATIONS

Ketterer, Biochem. J., vol. 96, No. 2, pp. 372–376, 1965.
Database Abstract WPI, Derwent Publication, AN. 91–373560/51 (JP 3 251544, Nov. 11, 1991).
Haginaka et al, *Journal of Chromatography*, vol. 592, pp. 301–307, 1992.
Haginaka et al, *Journal of Chromatography*, vol. 631, pp. 183–190, 1993.
Haginaka et al, *Journal of Chromatography*, vol. 620, pp. 199–204, 1993.
Haginaka et al, *Journal of Chromatography*, vol. 660, pp. 275–281, 1994.
Haginaka et al, *Anal. Chem.*, vol. 67, No. 15, pp. 2539–2547, Aug., 1995.
Archives of Biochemistry and Biophysics, vol. 160, No. 1, pp. 26–39, 1974, Theodore R. Oegama, Jr., et al., "The Physical and Chemical Properties of a Chicken Egg White Glycoprotein Purified by Nondenaturing Methodology".
Biochem. J., vol. 96, No. 2, pp. 372–376, 1965, B. Ketterer, "Ovoglycoprotein, A Protein of Hen's–Egg White".

*Primary Examiner*—Cecilia J. Tsang
*Assistant Examiner*—Abdel A. Mohamed
*Attorney, Agent, or Firm*—Oblon, Spivak, McClelland, Maier & Neustadt, P.C.

[57] ABSTRACT

An ovoglycoprotein has a molecular weight of 30,000 daltons which is determined by a matrix-assisted laser desorption ionization time-of-flight type mass spectrometer, an amino acid sequence of 15 residues from the N-terminal represented by Thr-Glu-Ser-Pro-Xaa-Ser-Ala-Pro-Leu-Val-Pro-Ala-Asp-Met-Asp (wherein Xaa represents a cysteine residue or an amino acid residue having a sugar chain linked thereto) (SEQ ID NO:1) and a sugar content of about 25% by weight and free of trypsin-inhibitory activity and a resolution agent for chromatography comprises a fixed phase which comprises a carrier and the foregoing ovoglycoprotein linked to the carrier. The agent for resolving optical isomers is not expensive, and is stable and highly resistant to deterioration by organic solvents, excellent in liquid-flow through properties, has a high sample-loading rate and permits efficient resolution of optical isomers of a chiral compound.

10 Claims, 7 Drawing Sheets

TIME (min.)

TIME (min.)

OVOGLYCOPROTEIN AND AGENTS FOR CHROMATOGRAPHIC SEPARATION CONTAINING SAME

BACKGROUND OF THE INVENTION

The present invention relates to a novel ovoglycoprotein and an agent for chromatographic separation and more specifically to an ovoglycoprotein having optical recognizability and an agent serving as a fixed phase for chromatographic separation comprising a carrier and the ovoglycoprotein linked to the carrier.

There has been strongly desired for the development of techniques for resolution of optical isomers of a chiral compound having an asymmetric carbon atom, in particular, in the field of medicines. This is because it has been proved, as a common knowledge, that one of the plurality of optical isomers constituting a racemic body exhibits particularly excellent medical effectiveness such as noticeable pharmacological action and/or marked bioavailability or exhibits, on the contrary, conspicuous toxicity and it has often been observed that such a medicine is reasonably administered to patients in the form of an optical isomer thus resolved rather than in the form of the racemic body thereof and that this often results in a high therapeutic effect.

There have conventionally been reported many laboratorial methods for resolving optical isomers, but most of these methods cannot be practiced in an industrial scale and it has been believed that the development of such a method capable of being practiced in an industrial scale is a quite difficult technical subject to be solved. As the column chromatography technique has been advanced, however, there have gradually been known methods for resolving optical isomers through, in particular, the liquid chromatography and examples thereof are disclosed in the articles 1) to 7) listed below:

1) Joergen Hermansson, Journal of Chromatography, 1985, 325, pp. 379–384;
2) S. Allenmark et al., Journal of Chromatography, 1983, 264, pp. 63–68;
3) S. Allenmark et al., Journal of Chromatography, 1982, 237, pp. 473–477;
4) Japanese Un-Examined Patent Publication No. Sho 60–41619;
5) T. Miwa et al., Chemical and Pharmaceutical Bulletin, 1987, 35, pp. 682–686;
6) J. Haginaka et al., Chromatographia, 1990, 29, pp. 587–592; and
7) Japanese Un-Examined Patent Publication No. Sho 64–3129.

Among the foregoing articles, Article 1) discloses a technique which makes use of a chiral acidic $\alpha_1$-glycoprotein. Articles 2) and 3) disclose methods for resolving optical isomers which make use of fixed phases comprising bovine serum albumin liked to silica and Agarose respectively. Article 4) discloses a method for resolving optical isomers through the use of orosomucoid or a functional analogue thereof. Articles 5) and 6) disclose optical isomer-resolution methods through the use of a fixed phase comprising a carrier and ovomucoid linked to the carrier. Article 7) discloses an optical isomer-resolution method which makes use of a fixed phase comprising a carrier and avidin linked to the carrier.

However, the materials used in the techniques disclosed in Articles 1) to 4) and 7) are in general expensive. Moreover, the resolution methods disclosed therein mainly comprise liquid chromatographic processes wherein a large amount of an organic solvent is used and accordingly, the materials to be used must be stable or resistant to deterioration by the organic solvent, but substances such as albumin and orosomucoid cannot satisfactorily fulfill the foregoing requirement. In addition, an agent for resolving optical isomers which comprises an immobilized protein has only a low rate of sample-loading.

SUMMARY OF THE INVENTION

Accordingly, an object of the present invention is to provide a novel protein effective for resolving optical isomers of a chiral compound.

Another object of the present invention is to provide an agent for chromatographically resolving optical isomers of a chiral compound, which is not expensive, stable and highly resistant to deterioration by an organic solvent, has excellent optical recognizability and a high rate of sample-loading and permits efficient resolution of these optical isomers.

The inventors of this invention have conducted various studies to accomplish the foregoing objects. As a result, the inventors have found out that an ovoglycoprotein easily available from egg white is excellent in the optical recognizability, has a high sample-loading rate and is stable and resistant to deterioration by an organic solvent and thus have completed the present invention.

According to an aspect of the present invention, there is provided an ovoglycoprotein which has a molecular weight of about 30,000 as determined by a matrix-assisted laser desorption ionization time-of-flight type mass spectrometer, an amino acid sequence of 15 residues from the N-terminal represented by Thr-Glu-Ser-Pro-Xaa-Ser-Ala-Pro-Leu-Val-Pro-Ala-Asp-Met-Asp (wherein Xaa represents a cysteine residue or an amino acid residue having a sugar chain linked thereto) (SEQ ID NO:1) and a sugar content of about 25% by weight and free of trypsin-inhibitory activity.

According to another aspect of the present invention, there is provided a resolution agent for chromatography which comprises a fixed phase which comprises a carrier and the ovoglycoprotein whose molecular structure may be partially modified and linked to the carrier.

The agent for chromatographically resolving optical isomers, more specifically, comprises a fixed phase which comprises a carrier and the ovoglycoprotein linked to the carrier; or a carrier and an ovoglycoprotein immobilized to the carrier and whose molecular structure is partially modified; or a carrier and an ovoglycoprotein which is molecularly and partially modified and linked to the carrier.

DESCRIPTION OF THE PREFERRED EMBODIMENTS

The present invention will hereunder be described in more detail with reference to the preferred embodiments.

The ovoglycoprotein of the present invention can be prepared by the following methods.

Preparation of Ovoglycoprotein

1) Separation of Acetone-Precipitated Powder from Egg White

To 450 ml of egg white, there is added 900 ml of a 1:2 (v/v) mixture of 0.5M trichloroacetic acid/acetone (pH 3.5) and the resulting mixture is stirred at 4° for 4 hours. The mixture is centrifuged at 4° C. and 5000 rpm for 30 minutes to remove precipitates. To the supernatant, there is added two volumes of cold acetone and the mixture is stirred for 15 minutes, followed by centrifugation at 4° C. and 5000 rpm for one hour to remove the resulting supernatant. The resulting precipitates are dissolved in deionized and distilled water, then dialyzed over a whole day and night and lyophilized. The resulting acetone-precipitated powder as such is used in the following isolation.

2) Isolation of Ovoglycoprotein from the Acetone-Precipitated Powder

Figure 1:
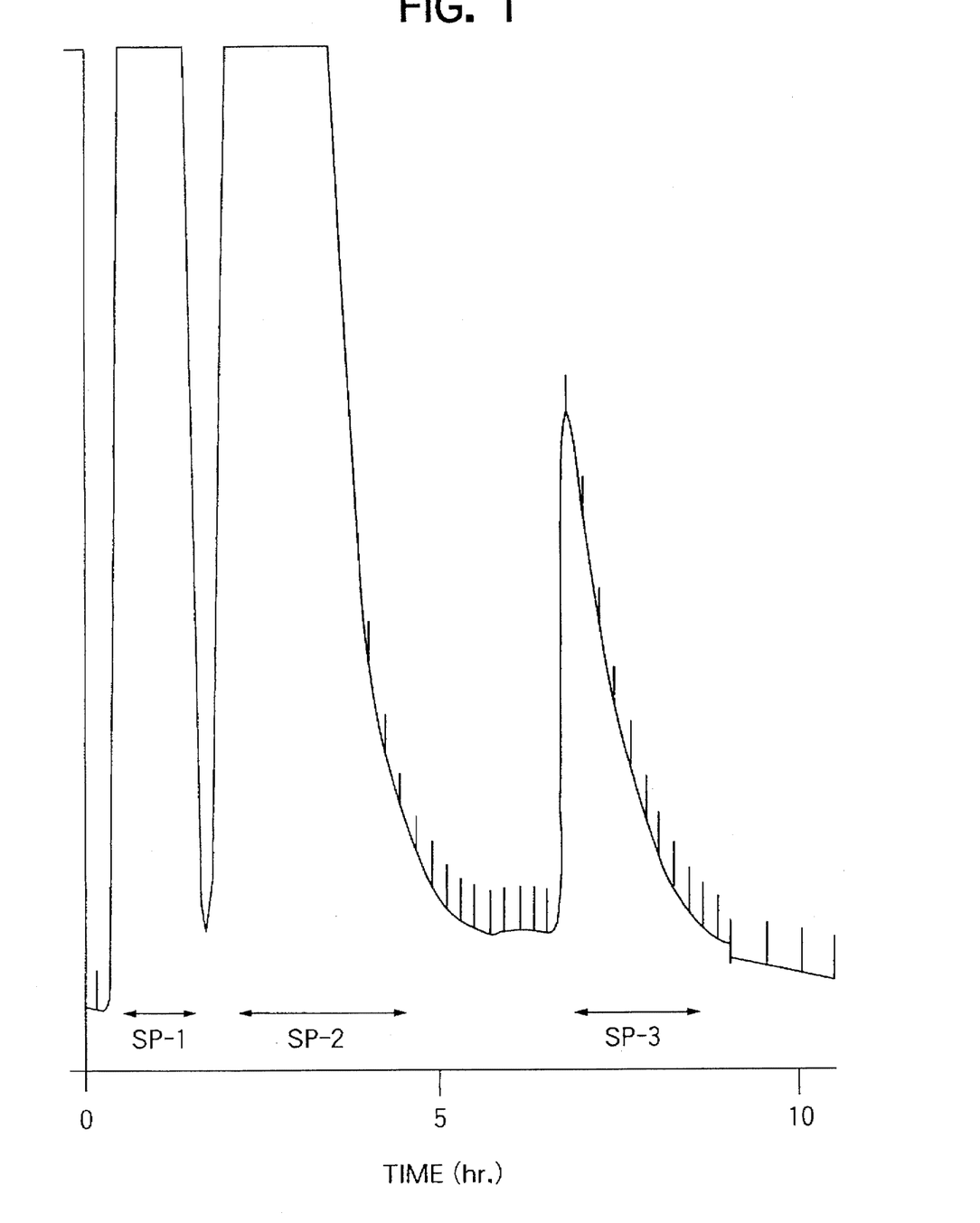
FIG. 1 shows a chromatogram illustrating the isolation of the ovoglycoprotein from acetone-precipitated powder of egg white.

The acetone-precipitated powder (about 3 g) is dissolved in 10 mM $CH_3COONH_4$ (pH 4.6) followed by filtration of the resulting solution. The filtrate is fractionated by ion-exchange chromatography to give fractions SP-1, SP-2 and SP-3. The chromatograms of the resulting fractions are shown in FIG. 1. Each of the fractions is desalted and then lyophilized. The conditions for the ion-exchange chromatography used are as follows:

Column:

SP-Sepharose (length: 6 cm; inner diameter: 5 cm)
Eluent:

Eluent A 250 ml of 10 mM $C_3COONH_4$ (pH 4.6);

Eluent B 250 ml of 500 mM $CH_3COONH_4$ (pH 4.6);

Eluent C 250 ml of 700 mM $CH_3COONH_4$ (pH 4.6)
(Eluents A and B are passed through the column over 5 hours according to the linear gradient elution technique and then Eluent C is passed therethrough).

Flow Rate: 100 ml/h

Detection: absorbance at 280 nm

Figure 2A:
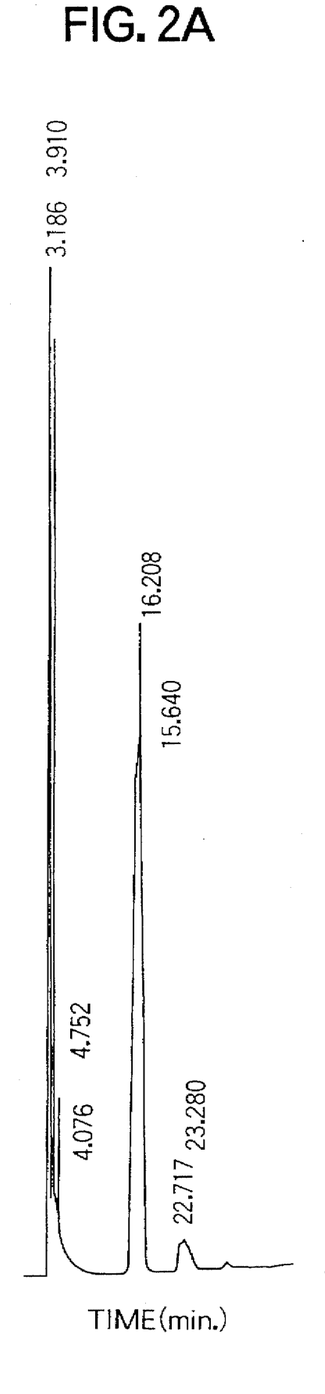
FIG. 2A, FIG. 2B and FIG. 2C shows chromatograms of fractions SP-1, SP-2 and SP-3 separated from acetone-precipitated powder of egg white.
Figure 2B:
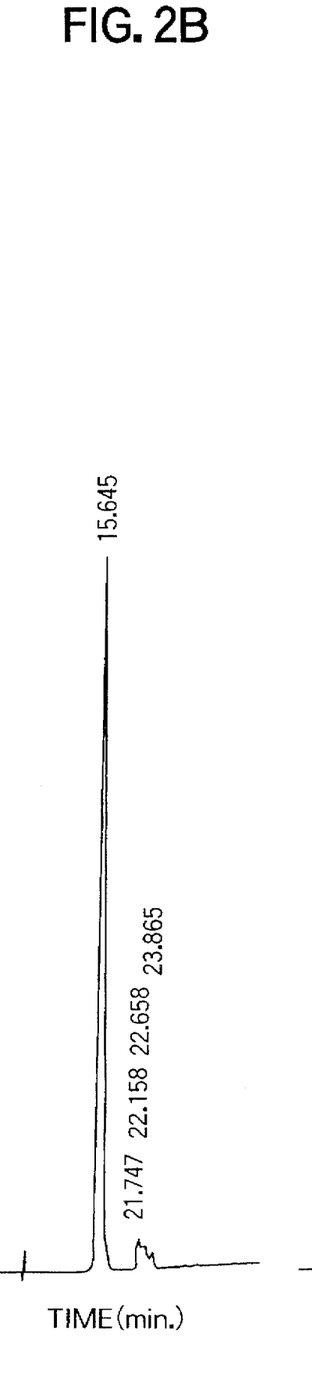
Figure 2C:
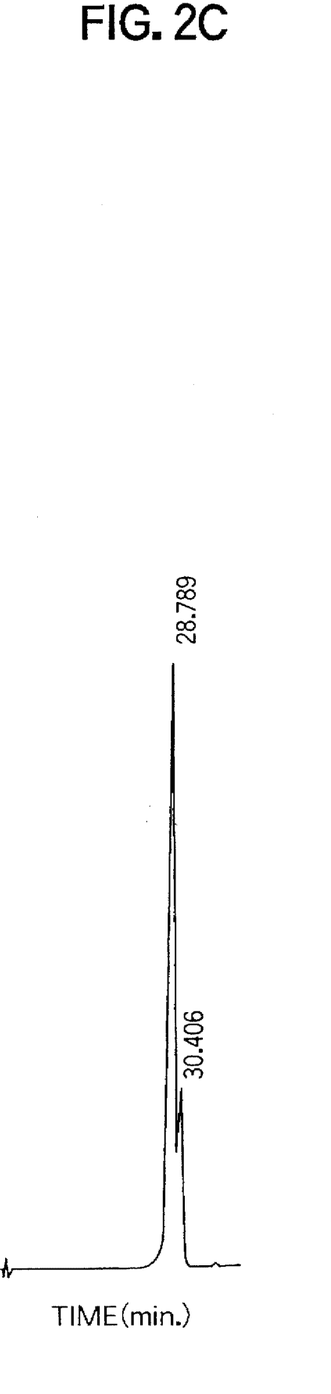

3) Reversed-Phase Liquid Chromatography of Ovoglycoprotein (FIG. 2)

In FIG. 2, A stands for the fraction SP-1, B the fraction SP-2 and C the fraction SP-3.:

The fraction SP-1 contained ovomucoid and an unidentified substance, the fraction SP-2 corresponded to ovomucoid and the fraction SP-3 was confirmed to be an ovoglycoprotein based on the results obtained in 4) as will be detailed below. The reversed-phase chromatography was performed under the following conditions:

Column:

Cosmosil 5C18-AR (length: 250 mm; inner diameter: 4.6 mm)

Eluent:

Eluent A $H_2O/CH_3CN$ (80/20, v/v) (containing 0.1% trifluoroacetic acid)

Eluent B $H_2O/CH_3CN$ (20/80, v/v) (containing 0.1% trifluoroacetic acid)

(Eluents are passed through the column starting from 0% Eluent B at the time zero to 100% Eluent B at the time 90 minutes according to a linear gradient elution technique).

Flow Rate: 1.0 ml/min

Detection: absorbance at 280 nm

4) Characteristic Properties of Fraction SP-3

(i) Molecular Weight of Fraction SP-3

Figure 3:
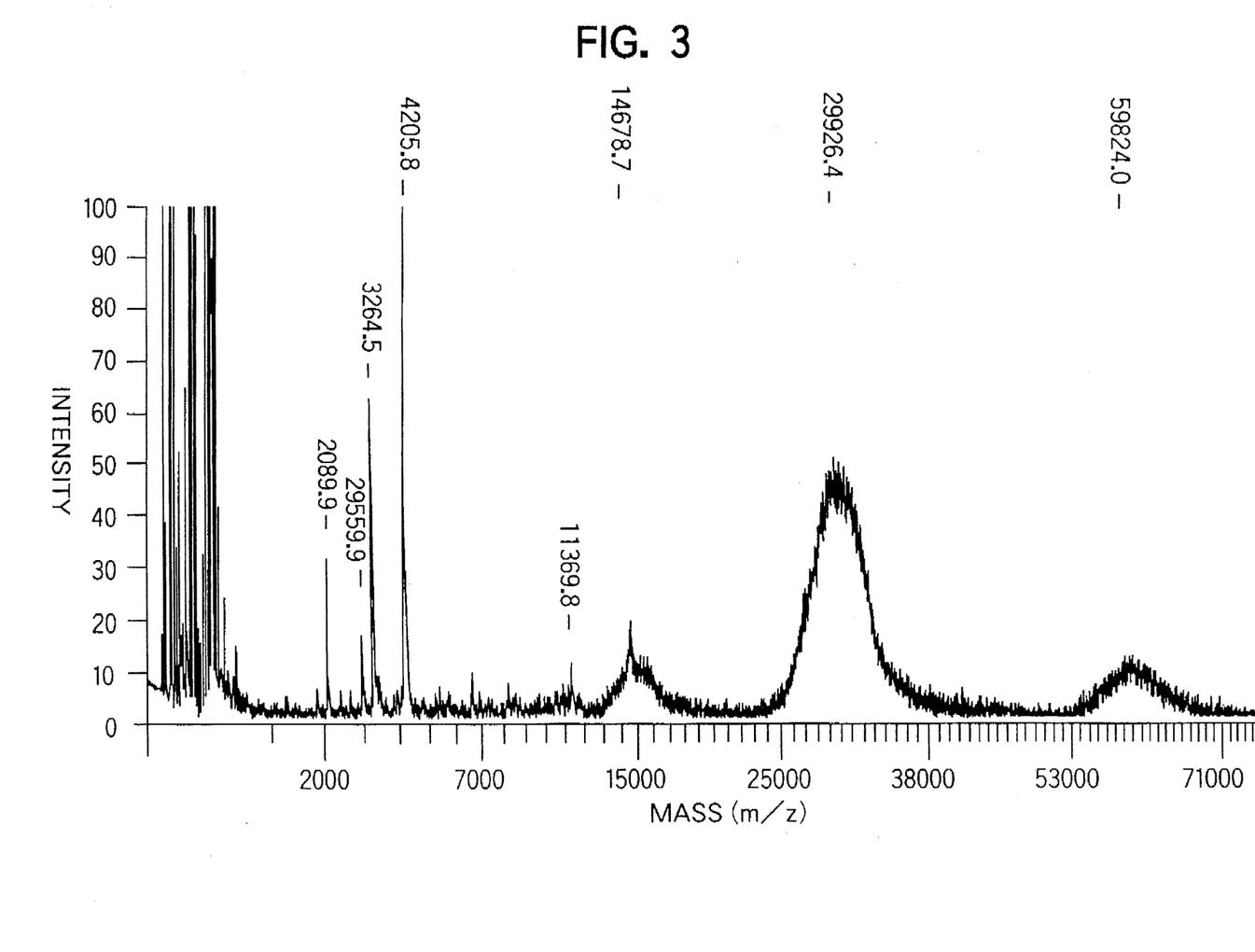
FIG. 3 shows a chart illustrating the results of the molecular weight analysis of the ovoglycoprotein performed by a mass spectrometer.

The molecular weight thereof was found to be about 30,000, which was determined by a matrix-assisted laser desorption ionization time-of-flight (MALDI-TOF) mass spectrometer (see FIG. 3).

(ii) Sugar Content of Fraction SP-3

The fraction SP-3 comprises 15.1% glucosamine, 7.3% hexose and 2.8% sialic acid and has a sugar content of about 25%.

(iii) Enzyme-Inhibitory Activity of Fraction SP-3

The fraction SP-3 does not show any trypsin-inhibitory activity.

(iv) N-Terminal Amino Acid Sequence of Fraction SP-3

The amino acid sequence of 15 residues from the N-terminal was found to be T-E-S-P-X-S-A-P-L-V-P-A-D-M-D (wherein X represents a cysteine residue or an amino acid residue having a sugar chain linked thereto)(SEQ ID NO140:1). As a result of search for amino acid sequences on the basis of the NBRF-PIR (National Biomedical Research Foundation Protein Information Resource) data base, it was confirmed that the foregoing amino acid sequence differs from the N-terminal amino acid sequence of the known ovomucoid and there was not found out any amino acid sequence identical or similar thereto. Accordingly, the fraction SP-3 was concluded to be a novel ovoglycoprotein.

The carrier used in the present invention may be any material which may be linked to the ovoglycoprotein whose molecular structure may partially be modified, to form a fixed phase. The agent for chromatographically resolving optical isomers according to the present invention is mainly used in the liquid chromatography. Examples of carriers for the agent applied to the liquid chromatography include silica gel, glass materials, cellulose, carbon materials and synthetic polymers.

The ovoglycoprotein can be linked to such a carrier by the method currently used for forming fixed phases, for instance, by a method which comprises linking the ovoglycoprotein to aminopropyl silica gel or a synthetic polymer having amino groups bonded thereto serving as a carrier while using N,N'-disuccinimidyl carbonate as a crosslinking agent; a method comprising linking the ovoglycoprotein to a glass material as a carrier using 3-glycidoxypropyl trimethoxysilane as a crosslinking agent; or a method comprising activating cellulose as a carrier with cyanogen bromide and then linking the ovoglycoprotein thereto.

Protein molecules are in general modified by a chemical, enzymatic or physical method. More specifically, a protein molecule may be chemically modified through reaction of amino, imidazolyl and/or carboxyl groups in the protein molecule with aldehyhdes, acid anhydrides and/or alcohols to thus form Schiff bases, N-substituted imidazolyl groups and/or ester residues. Alternatively, reactions such as modification of functional groups of the protein, oxidation and reduction of the protein molecule and/or elimination of a part of the molecule may be carried out under mild conditions while making use of the diversity of an enzyme in its functions.

For instance, the ovoglycoprotein which is partially modified with glutaraldehyde may be prepared by the following method.

The ovoglycoprotein and glutaraldehyde are introduced into a phosphate buffer (pH 6.8), followed by stirring at 30° C. for 15 hours and purification of the resulting ovoglycoprotein (non-reduced type) or an ovoglycoprotein (reduced type) obtained by optionally reducing the resulting glutaraldehyde-modified ovoglycoprotein (non-reduced type) with sodium borohydride in a phosphate buffer (pH 6.8) while stirring at 4° C. for 12 hours.

The purification method of the glutaraldehyde-modified ovoglycoprotein is not limited to a specific one and may be performed by any currently used one. For instance, the glutaraldehyde-modified ovoglycoprotein can be purified by removing the unreacted glutaraldehyde and sodium borohydride from the foregoing reaction solution through the use of Sephadex G25 column chromatography.

Moreover, an ovoglycoprotein which is partially modified with a diol can be obtained by adding the ovoglycoprotein and 2,3-epoxypropanol to a phosphate buffer (pH 8.0), stirring the mixture at room temperature for 24 hours and then purifying the reaction product.

In addition, an ovoglycoprotein partially acylated can be obtained by introducing the ovoglycoprotein and a corresponding acid anhydride such as acetic anhydride into a borate buffer (pH 8.5), stirring the mixture at 25° C. for 30 to 60 minutes and then purifying the resulting acylated ovoglycoprotein.

A fixed phase comprising a carrier and an ovoglycoprotein whose molecular structure is partially modified and linked to the carrier is prepared by, for instance, a method comprising linking an ovoglycoprotein whose molecular structure has, in advance, been partially modified to the carrier through covalent bonds or ionic bonds or a method comprising linking the ovoglycoprotein to the carrier and then modifying the ovoglycoprotein linked to the carrier by the method discussed above.

An ovoglycoprotein whose molecule is partially modified may be linked to a carrier, to give a fixed phase, by any method currently used for forming fixed phases. More specifically, ovoglycoprotein whose molecule is partially modified may be linked to a carrier by, for instance, preparing aminopropyl silica gel or a synthetic polymer carrying amino groups bonded thereto as a carrier and linking the ovoglycoprotein to the carrier through the use of glutaraldehyde or N,N'-disuccinimidyl carbonate as a crosslinking agent; by linking the ovoglycoprotein to silica gel or a glass or carbon material as a carrier while using 3-glycidoxypropyl trimethoxysilane as a crosslinking agent; or by activating cellulose as a carrier with cyanogen bromide and then linking the ovoglycoprotein thereto.

The glutaraldehyde-modified ovoglycoprotein can be linked to the aminopropyl silica gel carrier, for instance, by the following method.

The glutaraldehyde-modified ovoglycoprotein is dissolved in a sodium hydrogen carbonate buffer (pH 6.8). Separately, aminopropyl silica gel and N,N'-disuccinimidyl carbonate are dissolved or suspended in a sodium hydrogen carbonate buffer (pH 6.8), followed by stirring the reaction system overnight and preparative water-washing to give an activated aminopropyl silica gel suspension. The solution of the glutaraldehyde-modified ovoglycoprotein prepared above is added to the resulting activated aminopropyl silica gel suspension, followed by stirring the mixture and water-washing of the same to give an agent for resolving optical isomers of a chiral compound which comprises the glutaraldehyde-modified ovoglycoprotein linked to silica gel through the crosslinking agent.

The ovoglycoprotein linked to the carrier in advance can be chemically modified by the following method.

For instance, a carrier comprising a hydrophilic synthetic polymer (such as a polyvinyl alcohol copolymer) in which a polyamine such as pentaethylhexamine is introduced and N,N'-disuccinimidyl carbonate are dissolved or suspended in a sodium hydrogen carbonate buffer having a pH of 6.8, followed by stirring the mixture overnight and preparative water-washing of the same to give an activated synthetic polymer suspension.

Separately, the ovoglycoprotein is dissolved in a sodium hydrogen carbonate buffer having a pH of 6.8 to give a solution thereof and the solution is added to the activated synthetic polymer suspension to form a polymeric resolution agent to which the ovoglycoprotein is linked.

The resolution agent and glutaraldehyde are introduced into a phosphate buffer (pH 6.8), followed by stirring the mixture at 30° C. or 15 hours and optional reduction of the resulting glutaraldehyde-modified ovoglycoprotein (non-reduced type) with sodium borohydride in a phosphate buffer (pH 6.8) while stirring the reaction system at 4° C. for 12 hours to thus give an agent for resolving optical isomers comprising the glutaraldehyde-modified ovoglycoprotein (non-reduced type) or the glutaraldehyde-modified ovoglycoprotein (reduced type) which is linked to the synthetic polymer through amido bonds and the crosslinking agent. Such chemical modification of the ovoglycoprotein permits substantial improvement in the column life (number of sample-injections) of the column for resolving optical isomers in which the ovoglycoprotein is used in the form of a fixed phase.

As has been discussed above in detail, the present invention relates to the ovoglycoprotein or ovoglycoprotein whose molecular structure is partially modified, which is used in resolution of optical isomers of a chiral compound and is not particularly limited by, for instance, the kinds of carriers used, methods for linking the ovoglycoprotein to the carrier and/or methods for modifying the molecular structure thereof. The resolution agent of the present invention comprises the foregoing fixed phase as an essential component, but may simultaneously comprise appropriately selected conventional resolution agents such as silica gel, glass materials, cellulose, carbon materials and/or polymers, for the improvement in the resolution ability.

The term "optical isomers" used herein means chiral compounds each having an asymmetric carbon atom in the molecule and many medicines belong to such category of chiral compounds. Examples of such medicines are chlorpheniramine, chlorprenaline, pindolol, verapamil, propranolol, dimetindene, ethiazide, oxazepam and flurbiprofen. These compounds each comprises a plurality of optical isomers which are in the enantiomeric relation with each other and form a racemic body as a whole. In particular, the resolution agent of the present invention can effectively be applied to these racemic bodies to separate each racemic body into its optical isomers constituting the same.

The resolution agent of the invention is mainly used in the liquid chromatography. Therefore, the resolution agent may be employed according to the usual liquid chromatography operations. For instance, the resolution agent is packed in a column, a racemic body of the corresponding optical isomers is charged thereto, then a mobile phase comprising a buffering solution such as a phosphate buffer or a buffer comprising, for instance, ethanol or isopropanol is passed through the column to thus resolve the desired optical isomers based on the difference in the retention time between the optical isomers.

The present invention will hereunder be described in more detail with reference to the following non-limitative working Examples and the effects practically accomplished by the present invention will also be discussed in detail with reference to the following Test Examples.

Comparative Example 1

To 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, 2 g of the fraction SP-1 was dissolved in 30 ml of a 0.1M sodium hydrogen carbonate buffer (pH 6.8) to give a solution, followed by addition of the solution to the suspension prepared above to thus give a resolution agent carrying the immobilized SP-1 constituted by SP-1-linked silica gel. The resulting resolution agent was packed in a steel column to prepare a column for use in resolution of optical isomers.

Comparative Example 2

To 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, 2 g of the fraction SP-2 was dissolved in 30 ml of a 0.1M sodium hydrogen carbonate buffer (pH 6.8) to give a solution, followed by addition of the solution to the suspension prepared above to thus give a resolution agent carrying the immobilized SP-2 constituted by SP-2-linked silica gel. The resulting resolution agent was packed in a steel column to prepare a column for use in resolution of optical isomers.

Comparative Example 3

To 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, 2 g of commercially available ovomucoid was dissolved in 30 ml of a 0.1M sodium hydrogen carbonate buffer (pH 6.8) to give a solution, followed by addition of the solution to the suspension prepared above to thus give a resolution agent carrying the immobilized ovomucoid constituted by ovomucoid-linked silica gel. The resulting resolution agent was packed in a steel column to prepare a column for use in resolution of optical isomers.

EXAMPLE 1

To 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, 2 g of the ovoglycoprotein (the fraction SP-3) was dissolved in 30 ml of a 0.1M sodium hydrogen carbonate buffer (pH 6.8) to give a solution, followed by addition of the solution to the suspension prepared above to thus give a resolution agent carrying the immobilized ovoglycoprotein of the present invention constituted by ovoglycoprotein-linked silica gel. The resulting resolution agent was packed in a steel column to prepare a column for use in resolution of optical isomers.

EXAMPLE 2

To 0.06M phosphate buffer (pH 6.8), there were added 0.1 g of glutaraldehyde and 2 g of the ovoglycoprotein, followed by stirring the mixture at 30° C. for 15 hours to give an ovoglycoprotein modified with glutaraldehyde. Then the glutaraldehyde-modified ovoglycoprotein (non-reduced type) was isolated by treating the reaction system by Sephadex G25 column chromatography. The glutaraldehyde-modified ovoglycoprotein (non-reduced type) may further be reduced with sodium borohydrate at 4° C. for 12 hours in a phosphate buffer (pH 6.8) to give a glutaraldehyde-modified ovoglycoprotein (reduced type) and then purified.

To 100 ml of 0.1M sodium hydrogen carbonate buffer (pH 6.8), there were then added 2 g of a resolution agent for use in columns (such as Asahi Pack NH2P) in which a polyamine (such as pentaethylhexamine) was introduced into a hydrophilic polymer gel (polyvinyl alcohol copolymer) and 2 g of N,N'-disuccinimidyl carbonate, followed by stirring the mixture overnight, filtration through a glass filter and water-washing to give a suspension of an activated synthetic polymer gel. Separately, 2 g of a glutaraldehyde-modified ovoglycoprotein (reduced or non-reduced type one) was dissolved in 30 ml of a 0.1M sodium hydrogen carbonate buffer (pH 6.8) to give a solution, followed by addition of the solution to the suspension prepared above, stirring the mixture at 30° C. for 15 hours, filtration through a glass filter and water-washing to thus give a resolution agent of the present invention constituted by an glutaraldehyde-modified ovoglycoprotein-linked hydrophilic polymer gel. The resulting resolution agent was packed in a steel column to prepare a column for use in resolution of optical isomers.

EXAMPLE 3

To 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, 2 g of the ovoglycoprotein was dissolved in 30 ml of a 0.1M sodium hydrogen carbonate buffer (pH 6.8) to give a solution, followed by addition of the solution to the suspension prepared above to thus give a ovoglycoprotein-linked silica gel resolution agent. Then, to 30 ml of a 0.06M phosphate buffer (pH 6.8), there were added 2 g of the resolution agent and 0.1 g of glutaraldehyde, followed by stirring the mixture at 30° C. for 15 hours to give a resolution agent (non-reduced type) of the present invention. Further the resolution agent thus prepared was reduced by adding 0.2 g of sodium borohydride and stirring at 4° C. for 12 hours to give a resolution agent of the present invention comprising glutaraldehyde-modified ovoglycoprotein (reduced type)-linked silica gel. The resulting resolution agent was packed in a steel column to prepare a column for use in resolution of optical isomers.

EXAMPLE 4

To 100 ml of a 0.06M phosphate buffer (pH 6.8), there were added 3 g of aminopropyl silica gel and 0.1 g of glutaraldehyde, followed by stirring the mixture at 30° C. for 15 hours, filtration through a glass filter and water-washing to give glutaraldehyde-modified silica gel. To 30 ml of a 0.1M sodium hydrogen carbonate buffer (pH 6.8), there were added the glutaraldehyde-modified silica gel thus prepared and 2 g of the ovoglycoprotein to dissolve the ovoglycoprotein therein and react it with the former and to simultaneously modify the ovoglycoprotein with glutaraldehyde to thus give a resolution agent of the present invention comprising glutaraldehyde-modified ovoglycoprotein-linked silica gel. The resulting resolution agent was packed in a steel column to prepare a column for use in resolution of optical isomers.

EXAMPLE 5A

The same procedures used in Example 1 were repeated using aminopropyl silica gel to give a resolution agent comprising glutaraldehyde-modified ovoglycoprotein-linked silica gel. The resolution agent was dried in a desiccator packed with phosphorus pentoxide, then suspended in a 0.06M phosphate buffer (pH 8.0), followed by addition of 0.5 ml of 2,3-epoxypropanol and stirring at room temperature for 24 hours to give a resolution agent of the present invention comprising diol-modified ovoglycoprotein-linked silica gel. The resulting resolution agent was packed in a steel column to prepare a column for use in resolution of optical isomers.

EXAMPLE 5B

The ovoglycoprotein (2 g) was suspended in a 0.06M phosphate buffer, followed by addition of 0.5 ml of 2,3-epoxypropanol and stirring the mixture at room temperature for 24 hours to give an diol-modified ovoglycoprotein. Then, to 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, 2 g of the diol-modified ovoglycoprotein prepared above was dissolved in 30 ml of a 0.1M sodium hydrogen carbonate buffer (pH 6.8) to give a solution, followed by addition of the solution to the suspension prepared above, stirring the mixture at 30° C. for 15 hours, filtration through a glass filter and water-washing to thus give a resolution agent of the present invention constituted by diol-modified ovoglycoprotein-linked silica gel. The resulting resolution agent was packed in a steel column to prepare a column for use in resolution of optical isomers.

EXAMPLE 6A

The same procedures used in Example 1 were repeated using aminopropyl silica gel to give a resolution agent comprising ovoglycoprotein-linked silica gel. To 50 ml of a 0.1M borate buffer (pH 8.5), there were added 1.8 g of the resulting resolution agent and a solution of acetic anhydride (0.225 ml) in dioxane (1 ml), followed by stirring the mixture at 25° C. for 30 minutes, filtration through a glass filter and water-washing to thus give a resolution agent of the present invention constituted by acetylated ovoglycoprotein-linked silica gel. The resulting resolution agent was packed in a steel column to prepare a column for use in resolution of optical isomers.

EXAMPLE 6B

To a 0.1M borate buffer (pH 8.5), there were added 2 g of the ovoglycoprotein and a solution of acetic anhydride (0.225 ml) in dioxane (1 ml), followed by stirring the mixture at 25° C. for 30 minutes to give an acetylated ovoglycoprotein. Then, to 100 ml of a 0.1M sodium hydrogen carbonate buffer (pH 6.8), there were added 3 g of aminopropyl silica gel and 2 g of N,N'-disuccinimidyl carbonate, followed by stirring the mixture overnight, filtration through a glass filter and water-washing to give an activated aminopropyl silica gel suspension. Separately, the acetylated ovoglycoprotein (2 g) was dissolved in 30 ml of a 0.1M sodium hydrogen carbonate buffer (pH 6.8) to give a solution, followed by addition of the solution to the suspension prepared above to give a resolution agent of the present invention comprising acetylated ovoglycoprotein-linked silica gel. The resulting resolution agent was packed in a steel column to prepare a column for use in resolution of optical isomers.

The effects practically accomplished by the present invention will hereunder be discussed in detail with reference to the following Test Examples.

Test Example 1

Figure 4:
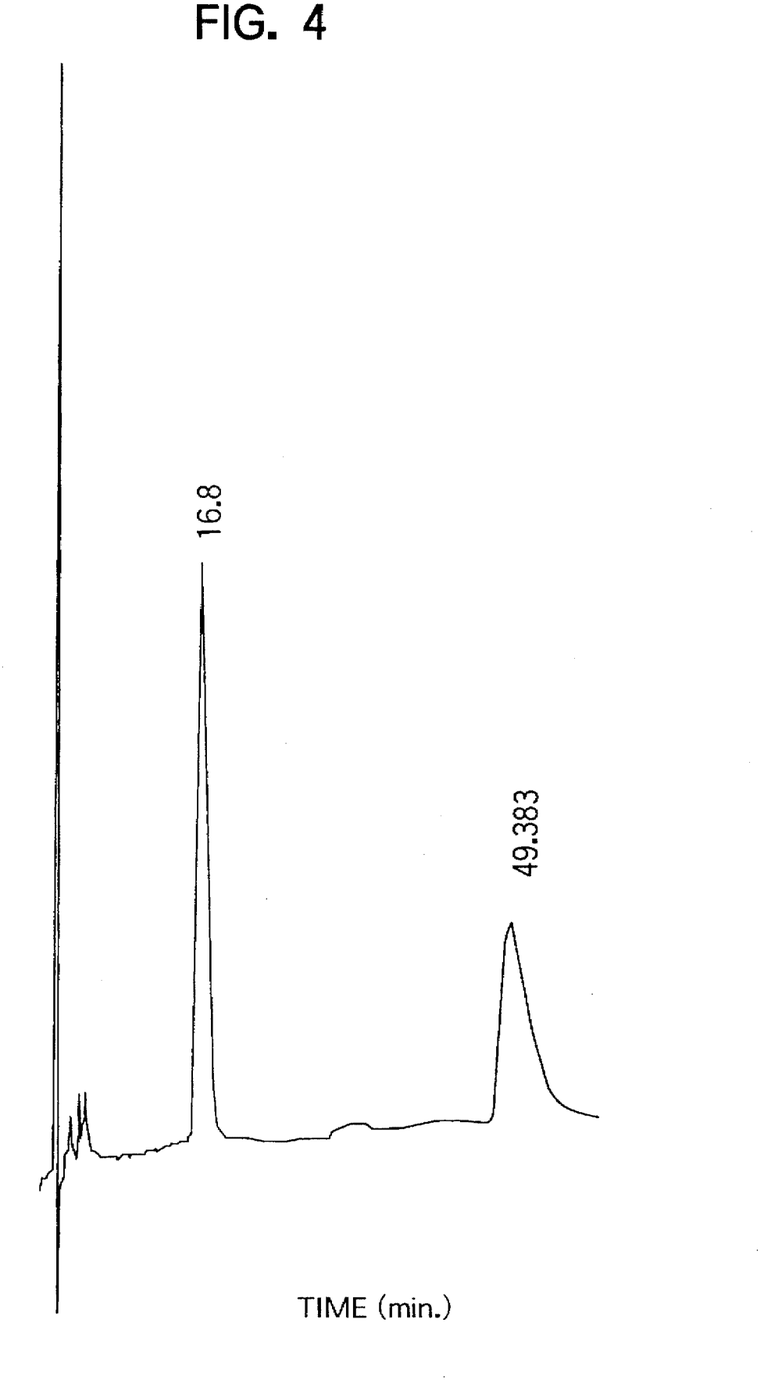
FIG. 4 shows a chromatogram illustrating the result obtained by resolving the enantiomer of benzoin using a column packed with an immobilized ovoglycoprotein.
Figure 5:
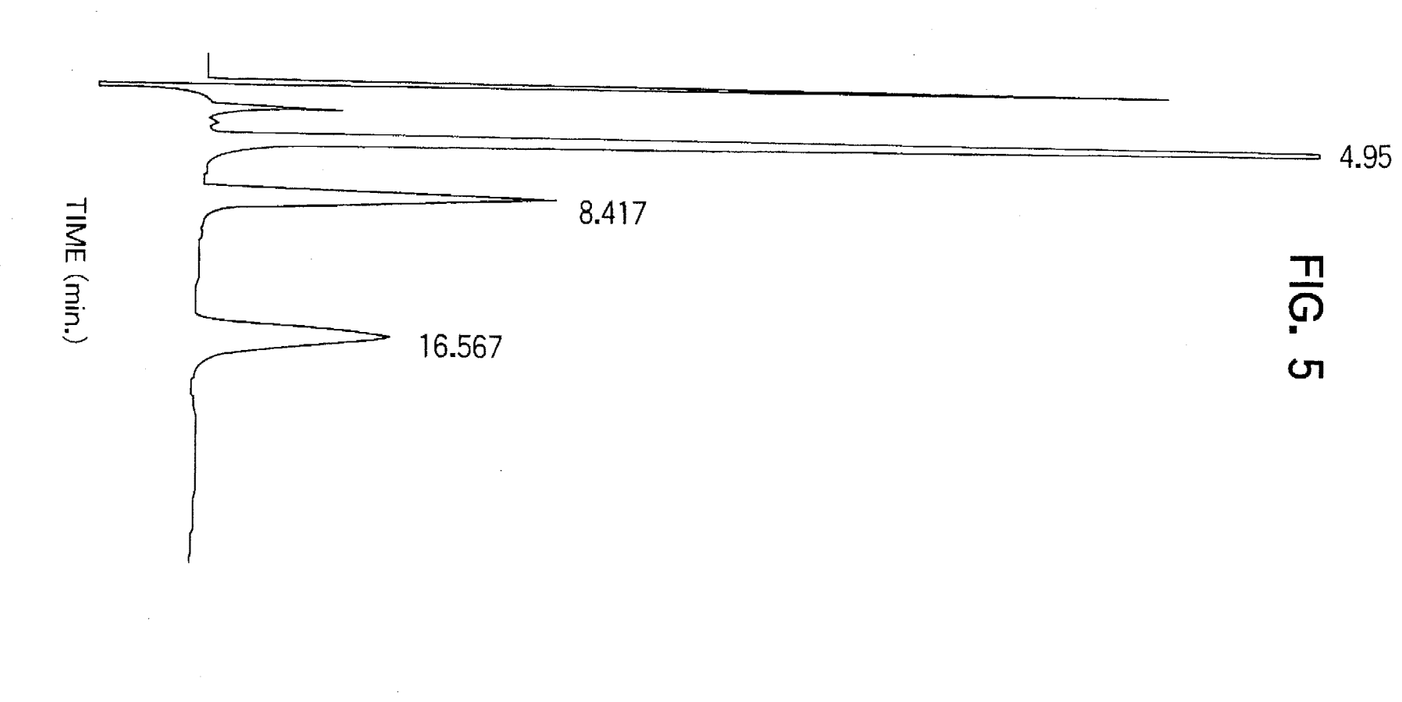
FIG. 5 shows a chromatogram illustrating the result obtained by resolving the enantiomer of chlorpheniramine maleate using a column packed with an immobilized ovoglycoprotein.
Figure 6:
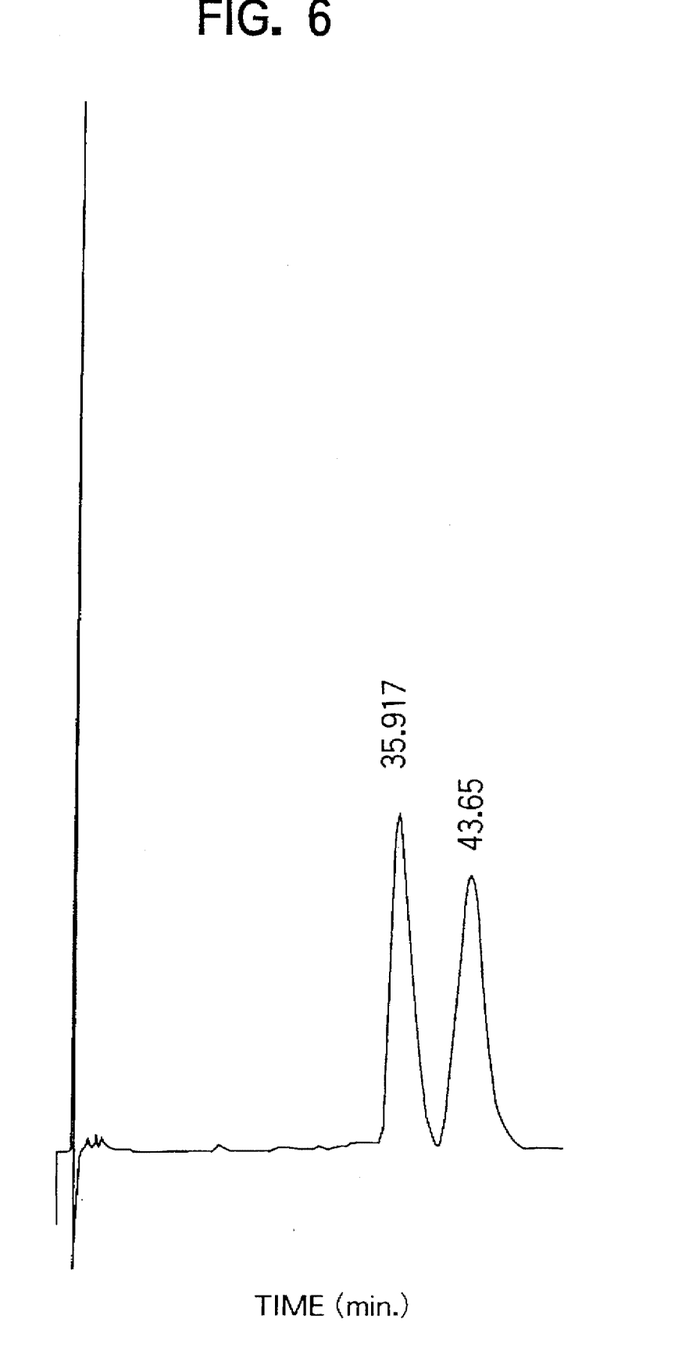
FIG. 6 shows a chromatogram illustrating the result obtained by resolving the enantiomer of ketoprofen using a column packed with an immobilized ovoglycoprotein.

Resolution of the isomers of benzoin, chlorpheniramine maleate or ketoprofen was carried out using the columns for resolution of optical isomers prepared in Comparative Examples 1 and 2 and Example 1. As a result, it was found that the column packed with the immobilized ovoglycoprotein (SP-3) exhibited an excellent resolution ability (see FIGS. 4, 5 and 6) and that the columns packed with the immobilized fractions SP-1 and SP-2 did not exhibit any optical recognizability.

In this respect, the HPLC was carried out under the following conditions: column used having an inner diameter of 2.0 mm and a length of 100 mm; mobile phase: 20 mM phosphate buffer (pH 5.1)/ethanol=90/10 (v/v); column temperature: 25° C.; flow rate: 0.2 ml/min; and detection: 220 nm.

Test Example 2

Figure 7A:
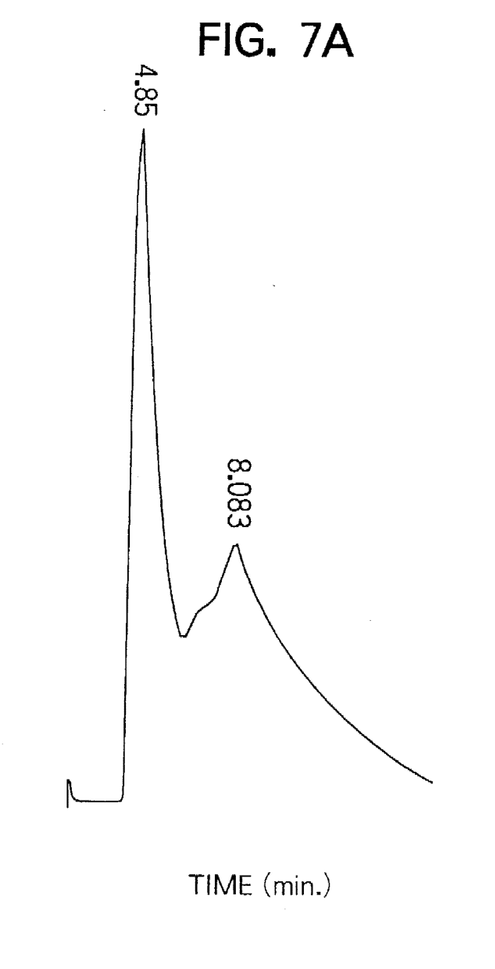
FIG. 7A and FIG. 7B shows a chromatogram illustrating the result of the test for sample-loading rate observed in the resolution of the enantiomer of benzoin.
Figure 7B:
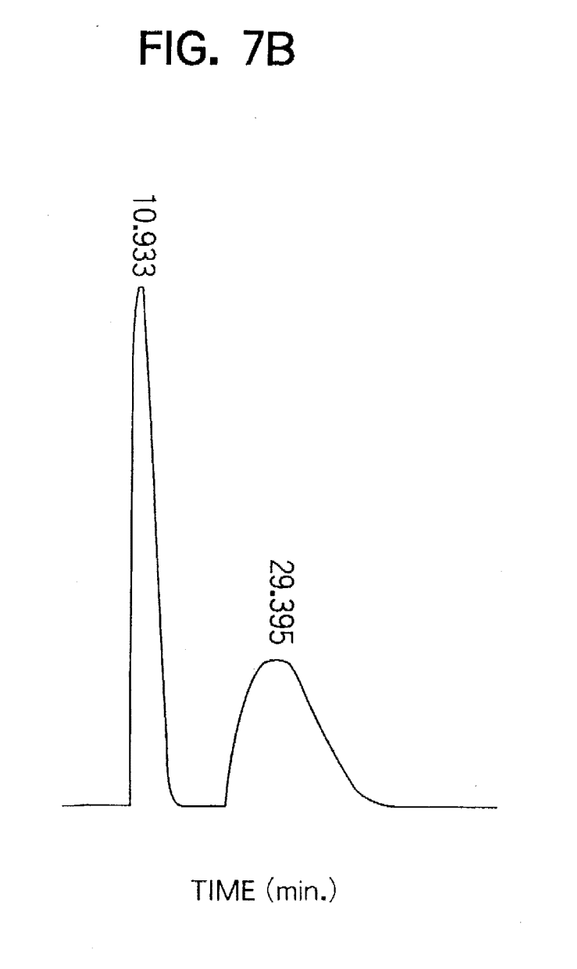

In this Test Example, the rate of sample-loading was examined by resolving the enantiomer of benzoin in the same manner used in Test Example 1. The results obtained are plotted on FIG. 7. In FIG. 7, the columns used were packed with immobilized commercially available ovomucoid for the spectrum A (FIG. 7A) and with the immobilized ovoglycoprotein of the present invention for the spectrum B (FIG. 7B), respectively.

In this respect, the HPLC was carried out under the following conditions: column used having an inner diameter of 2.0 mm and a length of 100 mm; mobile phase: 20 mM phosphate buffer (pH 5.1)/ethanol=90/10 (v/v); column temperature: 25° C.; flow rate: 0.2 ml/min; and detection: 254 nm. The amount of the sample injected was 2.5 nM for A or 20 nM for B.

The results shown in FIG. 7 indicate that the immobilized ovoglycoprotein resolution agent (B) of the present invention (FIG. 7B) exhibited a sample-loading rate 8 times greater than that observed for the immobilized ovomucoid resolution agent (A) (FIG. 7A).

As has been discussed above in detail, the agent for resolving optical isomers of the present invention is inexpensive, stable and highly resistant to deterioration by organic solvents, excellent in the liquid-flow through properties, has a high sample-loading rate and permits efficient resolution of optical isomers.

What is claimed is:

1. An ovoglycoprotein having a molecular weight of about 30,000 daltons as determined by a matrix-assisted laser desorption ionization time-of-flight type mass spectrometer, an amino acid sequence of 15 residues from the N-terminal represented by Thr-Glu-Ser-Pro-Xaa-Ser-Ala-pro-Leu-Val-Pro-Ala-Asp-Met-Asp, (SEQ ID NO:1) wherein Xaa represents a cysteine residue or an amino acid residue having a sugar chain linked thereto, and a sugar content of about 15% hexosamine, about 7% hexose and about 3% sialic acid by weight and free of trypsin-inhibitory activity.

2. A resolution agent for chromatography comprising a fixed phase which comprises a carrier and the ovoglycoprotein as set forth in claim 1 linked to the carrier.

3. The resolution agent for chromatography of claim 2 wherein said resolution agent resolves optical isomers of a chiral compound.

4. The resolution agent for chromatography of claim 2 wherein the carrier is a member selected from the group consisting of silica gel, glass, cellulose, carbon and synthetic polymers.

5. The resolution agent for chromatography of claim 4 wherein said resolution agent resolves optical isomers of a chiral compound.

6. The resolution agent of claim 2 wherein the ovoglycoprotein is one whose molecular structure is partially modified to facilitate the linking of said ovoglycoprotein to said carrier.

7. The resolution agent for chromatography of claim 6 wherein the ovoglycoprotein whose molecular structure is partially modified is a member selected from the group consisting of glutaraldehyde-modified ovoglycoprotein, non-reduced type, glutaraldehyde-modified ovoglycoprotein, reduced type, diolmodified ovoglycoprotein and acylated ovoglycoprotein.

8. The resolution agent for chromatography of claim 7 wherein said resolution agent resolves optical isomers of a chiral compound.

9. The resolution agent for chromatography of claim 7 wherein the carrier is a member selected from the group consisting of silica gel, glass, cellulose, carbon and synthetic polymers.

10. The resolution agent for chromatography of claim 9 wherein said resolution agent resolves optical isomers of a chiral compound.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Modified-site
        ( B ) LOCATION: 5
        ( D ) OTHER INFORMATION: /note= "X represents a Cys residue
            or an amino acid esidue having a sugar chain linked
            thereto"

( x i ) SEQUENCE DESCRIPTION: SEQ ID NO:1:

```
Thr  Glu  Ser  Pro  Xaa  Ser  Ala  Pro  Leu  Val  Pro  Ala  Asp  Met  Asp
1                   5                        10                       15
```